US010799541B2

(12) United States Patent
Gamble et al.

(10) Patent No.: US 10,799,541 B2
(45) Date of Patent: Oct. 13, 2020

(54) BI-LAYER DUAL RELEASE PROBIOTIC TABLETS

(71) Applicant: PROBI USA, INC., Redmond, WA (US)

(72) Inventors: Timothy Gamble, Redmond, WA (US); Anthony Blanch, Redmond, WA (US)

(73) Assignee: PROBI USA, INC., Redmond, WA (US)

( * ) Notice: Subject to any disclaimer, the term of this patent is extended or adjusted under 35 U.S.C. 154(b) by 0 days.

(21) Appl. No.: 15/318,262

(22) PCT Filed: Jun. 29, 2015

(86) PCT No.: PCT/US2015/038254
§ 371 (c)(1),
(2) Date: Dec. 12, 2016

(87) PCT Pub. No.: WO2016/003870
PCT Pub. Date: Jan. 7, 2016

(65) Prior Publication Data
US 2017/0100442 A1 Apr. 13, 2017

Related U.S. Application Data

(60) Provisional application No. 62/019,717, filed on Jul. 1, 2014.

(51) Int. Cl.
A61K 35/745 (2015.01)
A61K 35/744 (2015.01)
A61K 9/00 (2006.01)
A61K 35/747 (2015.01)
A61K 38/44 (2006.01)
A61K 9/24 (2006.01)
A61K 9/20 (2006.01)

(52) U.S. Cl.
CPC .......... A61K 35/745 (2013.01); A61K 9/0053 (2013.01); A61K 9/209 (2013.01); A61K 9/2054 (2013.01); A61K 9/2095 (2013.01); A61K 35/744 (2013.01); A61K 35/747 (2013.01); A61K 38/446 (2013.01); C12Y 115/01001 (2013.01)

(58) Field of Classification Search
CPC ..... A61K 9/209; A61K 35/745; A61K 35/744
See application file for complete search history.

(56) References Cited

U.S. PATENT DOCUMENTS

| 5,744,134 A | 4/1998 | Paul |
| 6,004,534 A | 12/1999 | Langer et al. |
| 6,180,099 B1 | 1/2001 | Paul |
| 6,241,983 B1 | 6/2001 | Paul et al. |
| 6,254,886 B1 | 7/2001 | Fusca |
| 6,627,220 B2 | 9/2003 | Turner et al. |
| 6,696,057 B1 | 2/2004 | Bojrab |
| 6,797,266 B2 | 9/2004 | Naidu |
| 6,974,594 B2 | 12/2005 | Ko et al. |
| 7,025,998 B2 | 4/2006 | Senin et al. |
| 7,101,565 B2 | 9/2006 | Monte |
| 7,150,623 B2 | 12/2006 | Turner et al. |
| 7,214,396 B2 | 5/2007 | Rivier |
| 7,842,495 B2 | 11/2010 | Yarnahira et al. |
| 7,960,137 B2 | 6/2011 | Connolly et al. |
| 7,982,066 B2 | 7/2011 | Scheele |
| 8,007,777 B2 | 8/2011 | Borek et al. |
| 8,048,924 B2 | 11/2011 | Elovuribe et al. |
| 8,110,177 B2 | 2/2012 | Lin et al. |
| 8,168,170 B2 | 5/2012 | Myatt |
| 8,313,768 B2 | 11/2012 | Kriksunov et al. |
| 8,361,497 B2 | 1/2013 | Miller |
| 8,409,591 B2 | 4/2013 | Farmer et al. |
| 8,425,930 B2 | 4/2013 | Barboza et al. |
| 8,540,980 B2 | 9/2013 | London et al. |
| 8,545,836 B2 | 10/2013 | Kaul et al. |
| 8,697,126 B2 | 4/2014 | Chen et al. |
| 8,722,035 B2 | 5/2014 | Porubcan |
| 8,945,619 B2 | 2/2015 | Berner et al. |
| 9,248,095 B2 | 2/2016 | Chang et al. |

(Continued)

FOREIGN PATENT DOCUMENTS

| CN | 202427429 U | 9/2012 | |
| EP | 0742712 B1 * | 8/2001 | ............ A61K 9/209 |
| EP | 1514547 A1 | 3/2005 | |
| JP | 60-37953 A | 2/1985 | |
| JP | 2000-302694 A | 10/2000 | |
| WO | 2003/105848 A1 | 12/2003 | |

(Continued)

OTHER PUBLICATIONS

Cook, M. et al. ("Microencapsulation of probiotics for gastrointestinal delivery", J Controlled Release 162, 2012, pp. 56-67. (Year: 2012).*
Meng et al., Pharmaceutics. Textbook of Pharmaceutical Science for Adult Higher Education. Shanghai Scientific & Technical Publishers, Shanghai. p. 134, Sep. 2011.

Primary Examiner — Gina C Justice
(74) Attorney, Agent, or Firm — McCarter & English, LLP; Steven G. Davis; Yu Lu

(57) ABSTRACT

The present invention generally relates to dietary supplement and pharmaceutical formulations comprising layered acid protective oral dosage formulations comprising probiotics and provided as single unified or cohesive dosage form units. Each individual acid protective layer of the cohesive dosage form provides one of a different probiotic payload, a different release profile to target delivery of probiotic to a particular region in the gastrointestinal tract, or both different probiotic payloads and release profiles to target delivery of different probiotics to particular regions in the gastrointestinal tract.

18 Claims, 11 Drawing Sheets

(56) References Cited

U.S. PATENT DOCUMENTS

| | | |
|---|---|---|
| 2002/0044926 A1 | 4/2002 | Reid et al. |
| 2003/0012819 A1 | 1/2003 | Ko et al. |
| 2003/0059501 A1 | 3/2003 | Rivier |
| 2003/0118547 A1* | 6/2003 | Vandenberg ............ A61K 47/02 424/85.4 |
| 2003/0147857 A1 | 8/2003 | Monte |
| 2003/0175295 A1 | 9/2003 | Ticktin |
| 2004/0076614 A1 | 4/2004 | Schur |
| 2004/0086491 A2 | 5/2004 | Monte |
| 2004/0120931 A1 | 6/2004 | Myatt |
| 2004/0146564 A1 | 7/2004 | Subirade et al. |
| 2004/0156895 A1 | 8/2004 | Pruitt et al. |
| 2005/0019417 A1 | 1/2005 | Ko et al. |
| 2005/0152966 A1 | 7/2005 | Borek et al. |
| 2005/0153018 A1 | 7/2005 | Ubbink et al. |
| 2005/0260181 A1 | 11/2005 | Girsh |
| 2005/0266069 A1 | 12/2005 | Simmones et al. |
| 2006/0062773 A1 | 3/2006 | Davis et al. |
| 2006/0115465 A1 | 6/2006 | Macfarlane et al. |
| 2006/0134082 A1 | 6/2006 | Baillon et al. |
| 2006/0188563 A1 | 8/2006 | Sato et al. |
| 2007/0184111 A1 | 8/2007 | Harris et al. |
| 2007/0269515 A1 | 11/2007 | Henriksen et al. |
| 2008/0044481 A1 | 2/2008 | Harel |
| 2008/0171085 A1 | 7/2008 | Elnekave et al. |
| 2008/0219961 A1 | 9/2008 | Rudolph et al. |
| 2008/0226603 A1 | 9/2008 | Al-Gahzzewi et al. |
| 2008/0286253 A1 | 11/2008 | Mulhbacher et al. |
| 2009/0082316 A1 | 3/2009 | Cimiluca et al. |
| 2009/0162322 A1 | 6/2009 | Rudolph et al. |
| 2009/0214647 A1 | 8/2009 | Chen et al. |
| 2009/0274662 A1 | 11/2009 | Magowan et al. |
| 2010/0068268 A1 | 3/2010 | Rahmouni et al. |
| 2010/0226995 A1 | 9/2010 | DeBrouse |
| 2010/0239682 A1 | 9/2010 | Andremont et al. |
| 2010/0247489 A1 | 9/2010 | Saur-Brosch |
| 2010/0254949 A1 | 10/2010 | Barboza et al. |
| 2010/0255087 A1 | 10/2010 | Coulter |
| 2010/0330151 A1 | 12/2010 | Freeland et al. |
| 2011/0020497 A1 | 1/2011 | Steven et al. |
| 2011/0064708 A1 | 3/2011 | Farmer et al. |
| 2011/0086011 A1 | 4/2011 | Kasper et al. |
| 2011/0223248 A1 | 9/2011 | Ritter |
| 2011/0236480 A1 | 9/2011 | Ritter et al. |
| 2011/0256216 A1 | 10/2011 | Lefkowitz |
| 2011/0287072 A1 | 11/2011 | Ritter et al. |
| 2012/0021095 A1 | 1/2012 | Mogna et al. |
| 2012/0034200 A1* | 2/2012 | Porubcan ............ A61K 9/148 424/93.45 |
| 2012/0087902 A1* | 4/2012 | Rescigno ............ G01N 33/5047 424/93.45 |
| 2012/0183516 A1 | 7/2012 | Burcelin et al. |
| 2012/0276201 A1 | 11/2012 | Trachtman |
| 2012/0321709 A1 | 12/2012 | Woo et al. |
| 2013/0108731 A1 | 5/2013 | Scheele |
| 2013/0177612 A1 | 7/2013 | Ritter et al. |
| 2013/0244969 A1 | 9/2013 | Ritter et al. |
| 2013/0259834 A1 | 10/2013 | Klaenhammer et al. |
| 2013/0287896 A1 | 10/2013 | Harel et al. |
| 2013/0295227 A1 | 11/2013 | Ter Harr et al. |
| 2013/0296165 A1 | 11/2013 | Harel et al. |
| 2014/0017313 A1 | 1/2014 | Coulter et al. |
| 2014/0037743 A1 | 2/2014 | DeBrouse |
| 2014/0037785 A1 | 2/2014 | Barboza et al. |
| 2014/0065116 A1 | 3/2014 | Mogna et al. |
| 2014/0065218 A1 | 3/2014 | Lang et al. |
| 2014/0072621 A1 | 3/2014 | De La Motte et al. |
| 2014/0112985 A1 | 4/2014 | Bochenek et al. |
| 2014/0154312 A1 | 6/2014 | Gulati et al. |
| 2014/0167307 A1 | 6/2014 | Horton |
| 2014/0171479 A1* | 6/2014 | Shah .................... A61K 9/2013 514/415 |
| 2016/0000841 A1* | 1/2016 | Yamamoto ............ A61K 35/741 424/93.46 |
| 2016/0022592 A1* | 1/2016 | Kabadi ................ A61K 9/4808 424/463 |

FOREIGN PATENT DOCUMENTS

| | | | |
|---|---|---|---|
| WO | 2010/008879 A2 | 1/2010 | |
| WO | WO-2010008879 A2 * | 1/2010 | ........... A23G 34/123 |
| WO | WO-2010057036 A2 * | 5/2010 | ........... A61K 9/0065 |
| WO | WO-2014/152338 A1 | 9/2014 | |

\* cited by examiner

BI-LAYER DUAL RELEASE PROBIOTIC TABLETS

CROSS REFERENCE TO RELATED APPLICATION

This application claims the benefit of U.S. provisional patent application 62/019,717, filed Jul. 1, 2014, the contents of which are incorporated herein in their entirety.

FIELD OF THE INVENTION

The present invention generally relates to dietary supplement and pharmaceutical formulations comprising multi-layered and bi-layered acid protective oral dosage formulations comprising probiotics and provided as single unified or cohesive dosage form units. Each individual acid protective layer of the cohesive dosage form provides one of a different probiotic payload, a different release profile to target delivery of probiotic to a particular region in the gastrointestinal tract, or both different probiotic payloads and release profiles to target delivery of different probiotics to particular regions in the gastrointestinal tract.

BACKGROUND OF THE INVENTION

Conventional probiotic dosage forms provide a single mode or rate of release for the probiotic payload carried therein.

Various probiotic formulations and methods of making such formulations are known to those of skill in the art. For example, uniform controlled release probiotic formulations are disclosed in U.S. Pat. Nos. 8,540,980; 8,007,777; 7,150,623; and 6,627,220. The contents of these patents are specifically noted and are incorporated into this disclosure by this reference. Specifically, U.S. Pat. Nos. 8,540,980 and 8,007,777 relate to various probiotic pre-blend powders used to make various uniform single dosage form units having controlled or sustained release.

Humans and animals seeking the benefit of probiotic supplementation of distinct microbes located in different regions of the gastrointestinal tract using conventional probiotic dosage forms must: (1) ingest multiple dosage forms each specific to the targeted delivery of each particular microbe and gastrointestinal tract region of interest; or (2) take inefficient or less effective single dosage forms providing uniform release of distinct microbes. Thus, the inventors have determined that, in certain instances, uniform single unit dosage form formulations including a mixture or combination of various probiotics can result in an inefficient and less effective delivery of the probiotic payload.

Uniform mixed or combined heterogeneous probiotic payload dosage forms can result in inefficient delivery, for example, where certain microbes best suited for delivery to the upper gastrointestinal tract are instead delivered in whole or in part to the lower gastrointestinal tract; meanwhile, certain other microbes best suited for delivery to the lower gastrointestinal tract may be delivered in whole or in part to the upper gastrointestinal tract.

There exists a need for a dosage form unit that provides for the separate formulation and release of distinct probiotics. Further, there exists a need for a single cohesive layered acid protective dosage form unit to provide varied rates of release and targeted delivery of probiotics suited for distinct regions of the gastrointestinal tract, such as, for example the upper gastrointestinal tract and the lower gastrointestinal tract.

BRIEF SUMMARY OF THE INVENTION

The inventors have for the first time developed cohesive acid protective oral dosage formulations and dosage forms comprising distinct probiotics in the different layers, wherein each layer has the same or a different rate of release. The inventive layered oral dosage formulations can accomplish targeted delivery of distinct probiotics to different locations in the gastrointestinal tract, for example, the upper gastrointestinal tract, such as the mouth, esophagus, stomach, duodenum, jejunum, and proximal ileum and also the lower gastrointestinal tract, such as the distal ileum, colon, and anus, to achieve maximum effect.

Formulations of the present invention can be used to accomplish immediate, sustained, controlled, intermittent, pulsed, and/or targeted probiotics delivery to various locations within the gastrointestinal tract, thus delivering release of targeted probiotics over any of immediate, interval, pulsed, and/or sustained or extended periods of time. The inventors of the present invention have, for the first time, realized and made possible the combination of various acid protective probiotic pre-blend powders in separate layers to achieve delivery of distinct probiotic formulations together in a single unified or cohesive acid protective dosage form unit. The inventors of the present invention have also, for the first time, realized and made possible the combination of various acid protective probiotic pre-blend powders in separate layers to achieve delivery of distinct probiotic formulations having differing release profiles together in a single unified or cohesive acid protective dosage form unit.

Each layer of the acid protective formulation may contain a different probiotic or mix of probiotics, distinguishable at one or more of the genus, species, sub-species, and strain level. Each layer may be characterized as immediate or as having any one of varying levels of pulsed, sustained, extended, or controlled release. Each layer may be of a different size, or comprise a greater portion of the final dosage form, relative to one or more of the other layers. The inventors of the present invention found that dosage form unit cohesion between the multi-layer or bi-layer probiotic acid protective dosage forms of the present invention is preferably optimized by including similar or identical amounts of one or more similar or identical excipients in each layer of the dosage form. Thus, in preferred embodiments of the present invention, certain formulation components are shared across the various layer formulations.

The dosage forms of the present invention are acid protective, but each layer may include varying levels of acid protection. The varying levels of acid protection may facilitate customization of the layer release profiles for targeted delivery of probiotic payload.

Preferred embodiments of the present invention do not include any enteric coating. Because enteric coatings are not needed to realize the benefits of the present invention, the dosage forms described herein avoid the further manufacturing complexity and expense associated with inclusion of such enteric coating. Regardless, formulations of the present invention may include enteric coating, but enteric coating is not necessary.

The formulations of the present invention can be used to protect the probiotics from the harsh acid environment of the stomach.

The formulations of the present invention may be formed into layered tablets or caplets, or similar dosage forms, via direct compression. Each layer of the present invention formulations may comprise a loose powder material or mixture prior to compression. Upon final compression, embodiments of the present invention advantageously form single layered cohesive non-friable dosage form units resistant to layer separation. Each formulation layer of the present invention may be first compressed separately, or pre-compressed, and then again compressed together with one or more additional layers. Alternatively, the formulation layers may be compressed together in a single compression. Varying compression or compaction pressures may be used with respect to compressing each one of the layers and/or the entire formulation. The processes described here are examples only, and do not constitute an exclusive list of processes that may be used to make the invention.

DETAILED DESCRIPTION OF THE INVENTION

1. Formulation Components

Figure 1A:
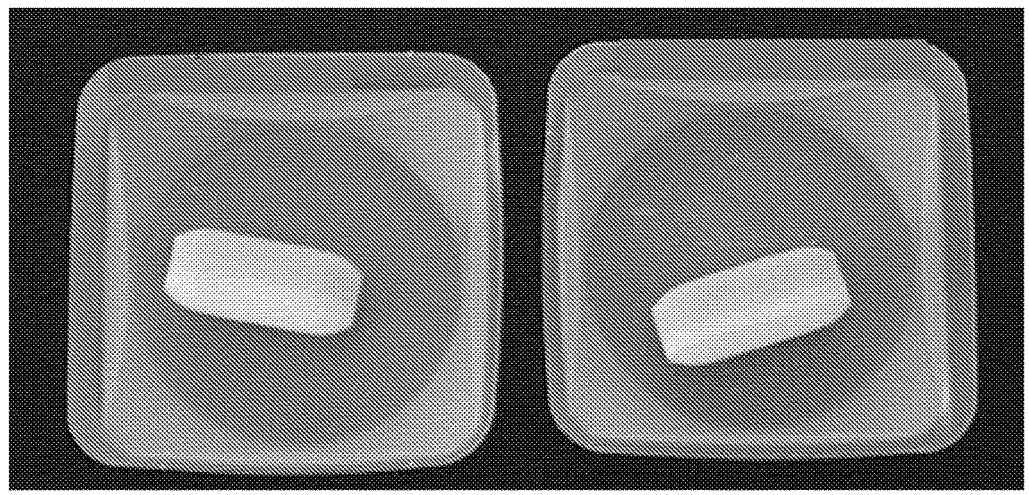
FIGS. 1A, 1B, 1C, and 1D show sustained release evaluation images of bi-layer tablets produced according to the present invention at zero, three, six, or nine hours, respectively, after exposure to acid (USP Type 2 apparatus, pH 2.5 at 37° C. with paddle stirring set at 50 RPM) followed by continued dissolution in a neutral solution.
Figure 1B:
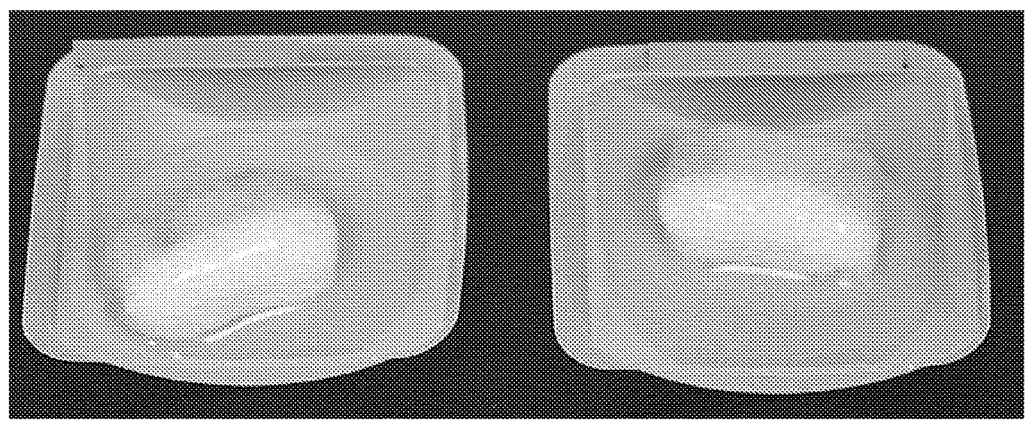
Figure 1C:
Figure 1D:
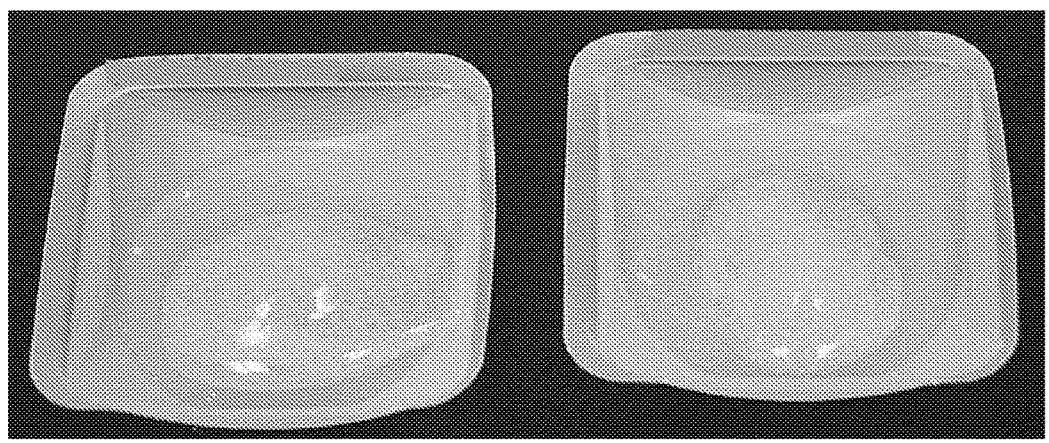

Probiotics of the present invention include, for example and without limitation, members of the genus *Lactobacillus, Bifidobacterium, Lactococcus, Enterococcus, Streptococcus, Pediococcus, Bacterioides*, or other organisms found to have probiotic effect, or portions, fragments, components, proteins, or by-products of such organisms. Specifically cultures of *Bifidobacterium animalis* subspecies *lactis, Bifidobacterium bifidum, Bifidobacterium breve, Bifidobacterium infantis, Bifidobacterium longum* (e.g., manufactured by DANISCO® vendor item codes 1217794 and 1244824, brand names BI-05 100B 1KG, BI-05 100B 20KG, probiotic viable count ≥1.0E+11 CFU/g; *Bifidobacterium longum* B1-05 SD-5588), *Enterococcus durans, Enterococcus faecium, Lactobacillus acidophilus, Lactobacillus brevis, Lactobacillus bulgaricus, Lactobacillus casei* subspecies *casei, Lactobacillus casei* subspecies *rhamnosus, Lactobacillus sakei, Lactobacillus fermentum* (e.g., manufactured by NUTRACEUTIX, probiotic viable count ≥5.0E+10 CFU/g, including non-GMO sourced material, including SD-5847), *Lactobacillus gasseri, Lactobacillus helveticus, Lactobacillus paracasei, Lactobacillus plantarum, Lactobacillus reuteri, Lactobacillus salivarius, Lactococcus lactis* subspecies *lactis, Pediococcus acidilactici, Pediococcus pentosaceus, Streptococcus thermophilus, Saccharomyces boulardii*, and various modified soil organisms. Probiotics of the present invention may include microorganisms not found in nature or probiotics otherwise altered to include foreign genetic or chemical material, including recombinant DNA. Probiotics of the present invention also include probiotic enzymes produced by, or derived or isolated from bacteria, and other probiotic by-products, including, for example, superoxide dismutase (SodA). Probiotics of the present invention can also include, optionally, non-viable cells or components or fragments thereof.

Each layer of the formulation may contain a different probiotic or mix of probiotics, distinguishable at one or more of the genus, species, sub-species, and strain level.

Formulations according to the present invention include one or more components that protect the probiotic payload from the deleterious effects of stomach acid. Such components include, for example, sodium carbonate, sodium bicarbonate, and sodium phosphate.

Additional components of the probiotic formulations include hydrophilic agents, such as, for example, swelling, viscosity increasing, gel strength enhancing agents. Hydrophilic agents may be selected from a group comprising, for example: starches (e.g., corn, rice, or potato starch), hydrophilic gum, polysaccharide or galactomannan (e.g., pectin, agar, dextran, carageenan, tragacanth gum, locust beam gum, acacia gum, guar gum, xanthan gum, ghatti gum, alginic acid or sodium alginate), cellulose derivative (e.g., methylcellulose, carboxymethylcellulose, sodium starch glycollate, sodium or calcium carboxymethylcellulose, hydroxyethyl methylcellulose, ethylhydroxy ethylcellulose, ethylmethylcellulose, hydroxyethylcellulose, cellulose acetate phthalate or microcrystalline cellulose), silica (e.g., silicon dioxide, brand name PRIOSIL PS-200, manufactured by Glassven; CAS #7631-86-9), aluminum silicate, magnesium silicate, aluminum magnesium silicate, sodium silicate or feldspar, aluminum hydroxide, protein (e.g., gelatin or casein), polymera (e.g., acrylate, carboxypolymethylene, a polyalkylene glycol or polyvinylpyrrolidone), hydrophilic polymers (e.g., cellulose derivatives such as microcrystalline cellulose (MCC)) (e.g., CAS #9004-34-6; microcrystalline cellulose MCC 112 manufactured by Accent Microcell Private Ltd.; material may be sourced from wood pulp, and including non-GMO sources), hydroxypropyl methylcellulose (HPMC) (also known as Hypromellose) (e.g., METHOCEL® K100 PREMIUM manufactured by THE DOW CHEMICAL COMPANY; material may be sourced from wood pulp and cotton linters; CAS #9004-65-3), or hydroxypropyl cellulose (HPC), or gums and polysaccharides such as guar gum or maltodextrin. Combination materials, such as, for example, AVICEL® CE-15 (MCC) and guar gum manufactured by FMC Biopolymer may also be used, wherein each component is sourced from wood pulp and plant sources, respectively, and including non-GMO sources; (CAS #9004-34-6 and CAS #9004-30-0).

Hydrophobic agents including waxes and other inert materials, for example, such as ethylcellulose or carnauba wax, may also be used.

The present formulations may use the pH-specific swelling characteristics or site-specific enzyme degradation to customize the controlled release of probiotics. For example, one or more of the following components may be used, or its relative amount in the formulation adjusted: alginate, polysaccharides such as such as gelatin or collagen, guar gum, xanthan gum, pectin (e.g., sourced from citrus and apple peel, including non-GMO citrus and apple peel), heterogeneous protein mixtures, polypeptides, polysaccharides (e.g., PECTIN 150 SLOW SET manufactured by Herbstreith & Fox; CAS #9000-69-5), pectin and/or an alginate salt and galactomannan gums (e.g., guar gum, xanthan gum and/or locust bean gum), polyethylene derivatives (e.g., polyethylene oxide (PEO) and/or polyethylene glycol (PEG)), hydrolyzed proteins (e.g., gelatin and/or collagen), and polypeptides (e.g., gelatin, collagen, casein, or a heterogeneous protein mixture).

Additionally, electrolytes may be included such as, for example, sodium, potassium, sodium carbonate anhydrous (e.g., food grade sodium carbonate anhydrous, including CAS #497-19-8), or calcium salts, among others. Inclusion of physiologically acceptable electrolytes may produce a buffered environment that allows reconstitution and release to occur under optimal pH conditions for bacterial viability. Interaction between electrolytes and, for example, a hydrophilic agent may allow not only the pH-independent release of the probiotic, but also stabilizes internal pH of the dosage form. Maintaining a stable internal pH contributes to the stability of the probiotics.

Binders, some of which may serve a dual purpose in the formulations as noted above, may include HPMC, MCC, guar gum, pectin (as a cohesive binder), etc.

Additional optional ingredients include salts, desiccants, disintegration agents, flow and tubing agents, lubricants, and coloring agents. For example, physiologically acceptable salts may be introduced to the probiotics during lyophilization at a ratio of 1.0:0.1 to 1.0:25 probiotics to salt. Addition of the salts also helps maintain a constant pH within the dosage form itself and acts as a cryoprotectant during the freeze-drying process to help prevent cell lysing. Desiccants may include, for example, sodium carboxymethylcellulose, calcium carboxymethylcellulose, colloidal silica dioxide, and/or combinations thereof. Disintegration agents may include, for example, croscarmellose sodium sold as SOLUTAB® available from Blanver Farmoquimica LTDA and crosprovidone (insoluble polyvinylpyrrolidone) sold as KOLLIDON® available from BASF. Flow and tubing and lubricant agents may include, for example, magnesium stearate and stearic acid (e.g., STEARIC ACID TRISTAR 149). Coloring agents may include, for example turmeric (e.g. NO. 03255 TURMERIC CG 90).

2. Processes for Preparing the Formulations

The inventive formulations may be prepared by combining various powder mixtures, each mixture comprising one or more preselected probiotics. These mixtures may be compressed together into a layered dosage form by a single compression. Alternatively, the mixture used to form any one layer may be pre-compressed prior to combination with one or more additional layers. In one embodiment, the dosage form is a multi-layered tablet or caplet. In a preferred embodiment, the dosage form is a bi-layer tablet or caplet for oral administration. In another preferred embodiment, the dosage form is a bi-layer tablet formed by sequential direct compression on a two sided tablet press. Compression may involve the intentional use of cooling to avoid damaging the probiotics.

Powder mixtures used with the present invention are dry. The powder mixtures may include lyophilized probiotic pre-blends. Specifically, the moisture content of the powder mixtures prior to compressions does not exceed 5%. Finished dosage forms according to the present invention have a water content that does not exceed 0.275 Aw.

Processing of the tablet blends is accomplished at ambient room temperatures and humidity. Ideally, processing room temperature and humidity would not exceed 23° C./45RH, but very low humidity can lead to electrostatic issues and difficulty in blending and compression of dry ingredients. Storage of the bulk culture concentrates and finished bulk dose forms is maintained at or below −10° C. The in-process tablet blends are stored at refrigerated temperatures of 4-15° C. in sealed liners when tablets are not actively being manufactured.

Stability of the formulations described herein may be assessed using various tests and protocols. For example, and without limitation, the formulations may be preferably tested in real time over a period of 18 months and/or in an Ambient Stability Environment (17-20 degrees Celsius/ ≤50% relative humidity) for viable CFU after, for example, 1 day and then again after 120 days. Alternatively, for example, and without limitation, the formulations may be tested in real time over a period of 18 months and/or in an Ambient Stability Environment (25 degrees Celsius/60% relative humidity) for viable CFU after, for example, 1 day and then again after 120 days.

It is contemplated that stability should not be affected; however, the initial compression losses may be greater due to a multi- or two stage compression process.

Manufacturing probiotic bi-layer caplets or tablets may follow standard setup and instructions offered by press manufacturers for making bi-layer dosage forms. For example, a dual sided tablet press designed to incorporate two unique formula blends through a double compression process is assembled and filled with blends in each of the two feed hoppers. As processing begins, operators adjust the rotational speed, flow rate, compression force, and punch depth to introduce blend and compress it in the first stage (primary side) of the caplet. This side continues in the die to the second stage fill and compression (secondary side) to form a single tablet.

In one embodiment, relative amounts of tablet bi-layer weights of the primary side and secondary side may vary from approximately 60%:40% to 70%:30% depending on the press used and the tablet dies. In a particular embodiment, as shown in Example 1, the tablet bi-layer weights comprise approximately 67% of the total weight in the primary side compression and approximately 33% of the total weight in the secondary side compression. Once finished, the tablet is ejected from the press and the punch/die station continues its rotation back to the first stage to repeat the process.

3. Formulations

In addition to the general formulation parameters provided herein, formulations used in any layer, or either or both of individual sides (if a bi-layer tablet), or in each subcomponent (if a multi-layer tablet), of the present invention overlap with certain of the uniform individual dosage form unit formulations described in U.S. Pat. Nos. 8,540,980 and 8,007,777 (which relate to and/or describe the BIO-tract® formulations). For this reason, the present inventors include here prior art evidence and data relating to preparation of certain uniform acid protective varied release probiotic uniform dosage forms that they have since determined can be advantageously substantially redesigned, reconfigured, and repurposed to form the layered dosage forms of the present invention, wherein each layer comprises a distinct probiotic and, optionally, has a distinct release profile. See Examples 4-12 and FIGS. 2-10.

In a preferred embodiment, one or more individual layers or "sides" of the bi-layer tablet of the present invention may include 5-40% hydrophilic agent, 5-40% release modifying agent, and 1-40% electrolytes. Release time modifications will be achieved initially by use of varying input % and viscosities of the release agents.

For example, in one embodiment, a bi-layer tablet according to the present invention is provided having a target weight of about 923 mg, with a first layer accounting for about 621 mg and a second layer accounting for about 302 mg. It is contemplated that variations of this embodiment can be prepared wherein the first layer accounts for about 621 mg (±50 mg) and the second layer accounting for about 302 mg (±30 mg).

The inventors have also determined that including certain percentage (%) weight amounts (w/w) of certain identical ingredients in each layer contributes to the successful preparation of unified cohesive layered dosage forms and reduces or eliminates final dosage form friability. For example, for dosage forms designed primarily to provide distinct probiotics from separate layered dosage forms, it is optimal for layers to balance the primary side and the second side layers of a bi-layer tablet with the same relative percentage of all ingredients. The inventors have also determined that it is particularly important for formulations components such as HPMC, pectin, MCC, and probiotic powder pre-blend, to be present in relatively similar amounts on each side to best promote unit cohesion. Dosage form cohesion is important not only for product shelf acceptance, but the stability and functionality of dosage forms. This is because separated, broken, and split dosage forms are harder to handle, and physically result in smaller dosage mass sizes and increased amounts of surface area that are exposed to oxygen (stability) and/or gastrointestinal dissolution agents that can result in premature dissolution and inefficient or ineffective delivery of the probiotic payload.

In several bi-layer tablet formulations of the present invention, HPMC, pectin, MCC, and probiotic powder pre-blend, are major input components (w/w) in the finished dosage forms.

In one embodiment, the bi-layer tablet formulations of the present invention include identical, or substantially similar, relative percentage (w/w) amounts of one or more given formulation major input components, including but not limited to HPMC, pectin, MCC, and probiotic powder pre-blend, in each layer to aid preparation of a unified cohesive layered dosage form. For example, the relative percentage (w/w) amounts of a given formulation component in each side of a bi-layer tablet may be within about 20% of the other side, more preferably within about 15% of the other side, still more preferably within about 10% of the other side, and most preferably within about 5% of the other side, and optimally within about 1% of the other side.

It is noted that while the dosage forms of the present invention are most frequently referred to as bi-layer tablets herein, the present invention encompasses multi-layered formulations and all compressible orally ingestible dosage form types, such as tablets and caplets.

4. Targeted Release

Different populations of cultures preferentially inhabit different areas of the human gastrointestinal tract. For the purposes of a targeted release probiotic ingestible dose form, microorganisms inhabiting the oral cavity and esophagus regions are not part of this discussion. The microbial ecology of the small intestine (duodenum, jejunum, and ileum) is dominantly populated by, for example, *Lactobacillus* and *Streptococcus* species. The colon (ascending, transverse, and descending) comprises, for example, some strictly anaerobic microbial population dominated by *Bifidobacteria, Bacteroides,* and *Clostridium* as well as Enterobacteriaceae.

The human gastrointestinal tract is one of the first defense mechanisms to keep diseases at bay. The enzymes and acids in the stomach act to kill pathogens before they have a chance to infect and proliferate or cause disease. Probiotic cultures can be killed by exposure to stomach acids, digestive enzymes, and bile salts.

Cultures differ in their ability to resist these digestive agents, some being very sensitive and some being more resistant. Generally, however, significant loss of viable cells occurs in the stomach. Probiotic selection historically has focused on strains able to resist these agents and several effective delivery technologies exist to protect sensitive cultures past the digestive region of the gastrointestinal tract.

Many conventional powdered and liquid dose forms of probiotic products provide no acid protection to the culture dose and often rely on the native acid resistance of a culture to survive passage through the stomach. Many delivery technologies release their entire payload at the onset of the small intestine in a pH/enzyme dependent burst response. For cultures adapted to that environment this may be adequate, but for cultures sensitive to the oxygen potential of the upper small intestine, a burst or immediate release may result in viability loss. A better delivery system for cultures sensitive to oxygen potential of the upper small intestine would provide protection and release of viable cultures over later or extended durations into the lower gastrointestinal tract, including the colon.

In one embodiment, this invention relates to preparations of varying release profiles to deposit at least two divergent classes of probiotics preferentially into their intended microbial niches. For example, the present invention may deliver the *Lactobacillus* and *Streptococcus* in the small intestine, or upper gastrointestinal tract, and the strict anaerobes like Bifidobacteria further into the lower intestinal tract. Example formulations to demonstrate the concept include comparisons of immediate release solid doses as negative controls (no protection) of each culture and, for example, bi-layer tablets according to the present invention.

*Bifidobacterium infantis* is very sensitive to oxygen and acid exposure. For example, the *B. infantis* blend may be designed to have extended release duration and superior acid protection for example, for delivery to the lower gastrointestinal tract. Also, *Lactobacillus plantarum* is aero tolerant and acid resistant; this blend is designed for moderate acid protection and a shorter release profile for example, for delivery via orally ingestible dosage forms to the upper gastrointestinal tract.

In one embodiment of the present invention, bi-layer tablets of *B. infantis* blend in the primary side and *L. plantarum* in the secondary side can be evaluated for manufacturing compression loss and differential viable count release over time in dissolution. In another embodiment, bi-layer tablets of *B. lactus* blend in the primary side and *L. fermentum* in the secondary side can be evaluated for manufacturing compression loss and differential viable count release over time in dissolution.

Additionally, it is noted that additional mass of the primary, or first, layer or side of a bi-layer tablet relative to the secondary layer may influence acid survival. Accordingly, the above-noted bi-layer embodiments may be tested by comparing each probiotic in either the first or second layer to determine which layered dosage form offers the best overall survival rates.

Preferred combinations might release, for example, 25-70% of the solid dose weight of the small intestine formula between hours 3-7; and, for example, 35-90% of the colon formula between hours 6-12.

In certain bi-layer tablet embodiments, for example, between about 30-40% of the solid dose weight is delivered to the small intestine formula between hours 3-7, primarily from the primary first side. Subsequently, the remaining amount of the solid dose weight is delivered to the colon or lower intestinal tract between hours 6-12, primarily from the secondary side. In certain other bi-layer tablet embodiments, for example, between about 20-30% of the solid dose weight is delivered to the small intestine formula between hours 3-7, primarily from the primary first side. Subsequently, the remaining amount of the solid dose weight is delivered to the colon or lower intestinal tract between hours 6-12, primarily from the secondary side.

EXAMPLES

Example 1: Cohesive *B. Lactis* and *L. Fermentum* Bi-Layer Formulation and Preparation

TABLE 1

|  | mg input per side | % of side | function |
|---|---|---|---|
| Part A |  |  |  |
| *Bifidobacterium lactis* | 100.50 | 17% | Active |
| Microcrystalline Cellulose | 274.03 | 47% | Filler |
| HPMC, Methocel, Dow K100m premium | 67.00 | 11% | binder/polymer |
| Pectin (150 slow set) | 100.50 | 17% | release modifier |
| sodium carbonate anhydrous food grade | 10.72 | 2% | Salt |
| stearic acid (tristar 149) | 10.72 | 2% | lubricant |
| Avicel CE-15 | 13.40 | 2% | lubricant |
| Turmeric #3255 (color) | 1.68 | 0% | Color |
| silica dioxide | 6.70 | 1% | lubricant |
|  | 585.25 | 100% |  |
| Part B |  |  |  |
| *Lactobacillus fermentum* | 49.50 | 17% | Active |
| Microcrystalline Cellulose | 132.33 | 46% | Filler |
| HPMC, Methocel, Dow K100m premium | 33.00 | 12% | binder/polymer |

TABLE 1-continued

|  | mg input per side | % of side | function |
|---|---|---|---|
| Pectin (150 slow set) | 49.50 | 17% | release modifier |
| sodium carbonate anhydrous food grade | 5.28 | 2% | Salt |
| stearic acid (tristar 149) | 5.28 | 2% | lubricant |
| Avicel CE-15 | 6.60 | 2% | lubricant |
| silica dioxide | 3.33 | 1% | lubricant |
|  | 284.82 | 100% |  |

Bi-layer tablets made using the above formulations were prepared using a Manesty® Double-Sided Press with Pre-compression (mark IV model) bi-layer tablet press to incorporate two unique formula blends through a double compression process.

The die or punch size used is size 0.312×0.750 (Punch ID: D23). Bi-layer tablets can be manufactured using a turret speed of 1,000 pills per minute. The upper punch penetration includes an 8 mm rear and a 4 mm front. The first layer has a fill depth of about 0.531 (set point 0.377) and the second layer has a fill depth of about 0.564 (set point 0.394). Average punch pressures (lbs/in$^2$) are for the first layer, pre-compression at about 202 and main compression at about 738. Average punch pressures for the second layer are pre-compression at about 64 and main compression at about 2188. The final KP (kilopond) is about 10.7 KP (avg.). The friability of such bi-layer tablets is about 0.25%, wherein friability indicates broken pills or separation of layers.

Friability is a USP standard test for tablet durability: ten (10) tablets are weighed, then inserted into a tumbler of standard dimension and rotation speed and time, then weighed again. The loss is recorded as a percent. Loss of <1% is good for most supplements and exceptional for probiotics.

Here, the finished dosage form weight (w/w) is about 870 mg, with a target weight of about 923 mg, with a first layer accounting for about 621 mg and a second layer accounting for about 302 mg.

Example 2: Acid Protection Evaluation of Distinct Culture Tabletted Bi-Layer Formulations Survival of viable probiotic cultures was evaluated in a USP Type 2 dissolution apparatus for the fasting state test parameters of 30 minutes of exposure at pH 2.5 at 37° C. with paddle stirring set at 50 RPM. Each data point is an average of three individual dose tests individually replicated in 900 mL of dissolution medium. The dosage forms tested were those prepared according to Example 1.

The probiotic counts were completed on the residual caplet material at the end of exposure by gently lifting the hydrated caplet out of the chamber and processing them for plate count assay by gentle dilution and homogenizing in a stomacher blender followed by standard plate count assay to enumerate viable colony forming units.

To assess the survival of the probiotic in an unprotected state, lyophilized powdered cultures (used to manufacture the caplets) were assayed for viable count prior to acid exposure and 1 g of this material was hydrated in the dissolution medium in the apparatus and received the same exposure. After exposure, a sample was drawn from the medium and processed as above for viable counts.

Differential enumeration of the *B. lactis* and *L. fermentum* was made possible by the cultures' distinct colony appearance and reported as total recovered viable cells after adjustment for dilution factors. Survival was determined by dividing the post acid recovered CFU by the introduced CFU and expressed as a percentage. This was further expressed as a "Protection Factor" for the individual cultures by dividing the caplet survival percentage by the unprotected powders survival percentage.

TABLE 2

30 Minutes pH 2.5 at 37° C. 50 RPM

| Product & Lot no. | Pre-Dissolution CFU/cap | Post-Dissolution CFU/cap | Survival % | Protection Factor |
|---|---|---|---|---|
| Bi-layer Caplet/Tablet B. lactis count | 4.5E+09 | 3.0E+09 | 60.0 | 18X |
| Bi-layer Caplet/Tablet L. fermentum count | 2.3E+09 | 1.5E+09 | 73.9 | 1850X |

| | Pre-Dissolution CFU introduced | Post-Dissolution CFU recovered | | |
|---|---|---|---|---|
| Unprotected powder B. lactis count | 6.0E+11 | 2.0E+10 | 3.3% | |
| Unprotected powder L. fermentum count | 5.0E+11 | 2.0E+08 | 0.04% | |

*L. fermentum* is an acid sensitive culture, but it is targeted for delivery to the upper gastrointestinal tract such that it may be conventionally considered suitable for immediate release formulations or formulations that do not require prolonged or controlled release profiles. The data here shows severe losses in *L. fermentum* viability when *L. fermentum* was directly tested in acid, and marked avoidance or reduction of those losses when prepared in the acid protective present inventive dosage forms, such as those described in Example 1. These results highlight the critical need for acid protection during stomach passage even if the culture being administered is targeted for delivery to the upper gastrointestinal tract and, thus, not expected to need protection from stomach acid.

This series of tests demonstrates the superior protection of viable payload for each of the two divergent genera of probiotic cultures provided by the bi-layer tablet. Surprisingly, the *L. fermentum* culture, absent formulation according to the present invention, turned out to be extremely sensitive to acid. Indeed, the inventors found that the present inventive formulations provide a surprising formulation protection factor in excess of 1800× for the *L. fermentum* culture.

Here, even while the *Bifidobacterium* culture, *B. lactis*, ended up being orders of magnitude more acid resistant than the *L. fermentum* culture, both cultures benefited from the acid protection provided by the bi-layer tablet dosage form. The data here demonstrates an important advantage of using the acid protective formulations disclosed herein for all cultures regardless of whether the culture(s) incorporated into the formulation are more or less acid sensitive and regardless of whether the targeted delivery site is the upper gastrointestinal tract or the lower gastrointestinal tract.

Further, this example shows that the acid protective formulations of the present invention allow for the combination of disparate formulations containing, for example, sensitive or acid resistant cultures, together in a single cohesive dosage form that provides shared similar acid protection for transport of the dosage form probiotic payload past the stomach. Accordingly, this example shows that the acid protected layered dosage forms of present invention can facilitate the deposit of appropriate probiotics, including acid sensitive probiotics, to target sites located in distinct regions of the gastrointestinal tract.

Example 3: Sustained Release Evaluation

To demonstrate the sustained release of viable probiotic from those dosage forms prepared according to Example 1 through a simulated intestinal passage, the same USP Type 2 apparatus and testing parameters were used for the initial acid exposure as noted above in Example 2 (i.e., USP Type 2 dissolution apparatus for the fasting state test parameters of 30 minutes of exposure at pH 2.5 at 37° C. with paddle stirring set at 50 RPM). Then, at 30 minutes, the pH of the chambers was adjusted to neutrality pH 7.0-7.5 and the doses were allowed to remain in the chambers for additional dissolution exposure to a total time of 3, 6, or 9 hours. Images of the dosage forms prepared according to Example 1 are provided here as FIGS. 1A, 1B, 1C, and 1D for each of the zero time, 3 hour time, 6 hour time, and 9 hour time, respectively. At the end of the test period, the residual dosage form was gently removed from the chamber and processed as above to determine viable count remaining in the intact caplet. A sample of the dissolution medium was taken and assayed for probiotic viable count released in the medium. Counts were adjusted to reflect the total CFU introduced into and recovered from the dissolution chamber. Again, three replicates were tested for each data point and averaged in the reporting.

The data below shows a gradually increasing cell count recovery as the bi-layer tablet dissolves. The total recovery section at the bottom shows that the probiotics recovered gradually decline but, importantly, that cell recovery occurs and is present through at least about 9 hours of exposure.

TABLE 3

30 Minutes pH 2.5 at 37° C. 50 RPM followed by neutralization of media and continued dissolution

| Residual caplets assayed at: | Pre-Dissolution CFU/cap | Post-Dissolution CFU/cap | Survival % |
|---|---|---|---|
| 3 Hours- Total Count | 7.70E+09 | 1.6E+09 | 20.8% |
| 3 Hours- B. lactis Count | 4.5E+09 | 7.4E+08 | 16.5% |
| 3 Hours- L. fermentum Count | 2.3E+09 | 8.6E+08 | 37.2% |
| 6 Hours- Total Count | 7.70E+09 | 6.8E+08 | 8.8% |
| 6 Hours- B. lactis Count | 4.5E+09 | 2.7E+08 | 6.0% |
| 6 Hours- L. fermentum Count | 2.3E+09 | 4.1E+08 | 17.8% |
| 9 Hours- Total Count | 7.70E+09 | 1.5E+08 | 2.0% |
| 9 Hours- B. lactis Count | 4.5E+09 | 2.3E+07 | 0.5% |
| 9 Hours- L. fermentum Count | 2.3E+09 | 1.3E+08 | 5.7% |

| Dissolution medium assayed at: | Pre-Dissolution caplet CFU introduced | Post-Dissolution CFU recovered | Survival % |
|---|---|---|---|
| 3 Hours- Total Count | 7.70E+09 | 3.8E+08 | 5.6 |
| 3 Hours- B. lactis Count | 4.5E+09 | 1.8E+08 | 3.9 |
| 3 Hours- L. fermentum Count | 2.3E+09 | 2.1E+08 | 9.1 |
| 6 Hours- Total Count | 7.70E+09 | 1.2E+09 | 17.1 |
| 6 Hours- B. lactis Count | 4.5E+09 | 5.1E+08 | 11.2 |
| 6 Hours- L. fermentum Count | 2.3E+09 | 6.6E+08 | 28.6 |
| 9 Hours- Total Count | 7.70E+09 | 9.1E+08 | 13.3 |
| 9 Hours- B. lactis Count | 4.5E+09 | 3.9E+08 | 8.6 |
| 9 Hours- L. fermentum Count | 2.3E+09 | 5.2E+08 | 22.6 |

TABLE 3-continued

30 Minutes pH 2.5 at 37° C. 50 RPM followed
by neutralization of media and continued dissolution

| Total recovered viable count, Caplet + Medium | Pre-Dissolution caplet CFU introduced | Post-Dissolution CFU recovered | Total Survival % |
|---|---|---|---|
| 3 Hours- Total Count | 7.70E+09 | 2.0E+09 | 26% |
| 3 Hours- *B. lactis* Count | 4.5E+09 | 9.2E+08 | 20% |
| 3 Hours- *L. fermentum* Count | 2.3E+09 | 1.1E+09 | 46% |
| 6 Hours- Total Count | 7.70E+09 | 1.8E+09 | 24% |
| 6 Hours- *B. lactis* Count | 4.5E+09 | 7.7E+08 | 17% |
| 6 Hours- *L. fermentum* Count | 2.3E+09 | 1.1E+09 | 46% |
| 9 Hours- Total Count | 7.70E+09 | 1.1E+09 | 14% |
| 9 Hours- *B. lactis* Count | 4.5E+09 | 4.1E+08 | 9% |
| 9 Hours- *L. fermentum* Count | 2.3E+09 | 6.5E+08 | 28% |

The residual dosage forms demonstrated progressive reduction in viable count as the dosage forms eroded into the medium. The media samples progressively increased in count through the 9 hours tested. Importantly, viable cell recovery was sustained through 9 hours, with total recovery dropping from 66% of the initial dose at the 30 minute time point, to 26%, 24%, and 14% at 3, 6, and 9 hours respectively. It is noted that significant active cell counts were recovered throughout the dissolution.

The following Examples provide layer formulations proposed for use as subcomponents of the dosage forms of the present invention. These formulations taken alone are considered too small in total mass to work with many conventional layered tablet presses. It is noted that one way to increase total mass weight is, for example, including fillers, such as MCC or maltodextrin. It is noted, however, that while inclusion of MCC or maltodextrin may be important for tablet compression, these components generally do not aid tablet cohesion. Further, including large amounts of MCC or maltodextrin can affect the tablet release rate, i.e., increase the rate of release.

Preparation of the dosage forms of the present invention may comprise one or more of the following layer formulations taken together with other layer formulations as described herein to form the layered cohesive acid protective formulations of the present invention, to provide distinct probiotic layers and to provide distinct probiotic layers having distinct release profiles.

Example 4

One subcomponent of a multilayered dosage form, or side of a bi-layer tablet dosage form, weighing approximately 382 mg, and containing a hydrophilic agent and a probiotic pre-blend was prepared as shown in Table 4. The group A1 is the control. In this example, the probiotic pre-blend is comprised of beneficial microorganisms such as the lactic acid bacteria pre-blend of lyophilized powder and starch. The hydrophilic agent employed is microcrystalline cellulose (MCC), maltodextrin, hydroxypropyl methylcellulose (HPMC), or polyethylene oxide (PEO). The addition of the hydrophilic agent will retard the release of the probiotic from the dosage form. Stearic acid is included as a flow agent and silica is employed as flow agent and desiccant.

Figure 2:
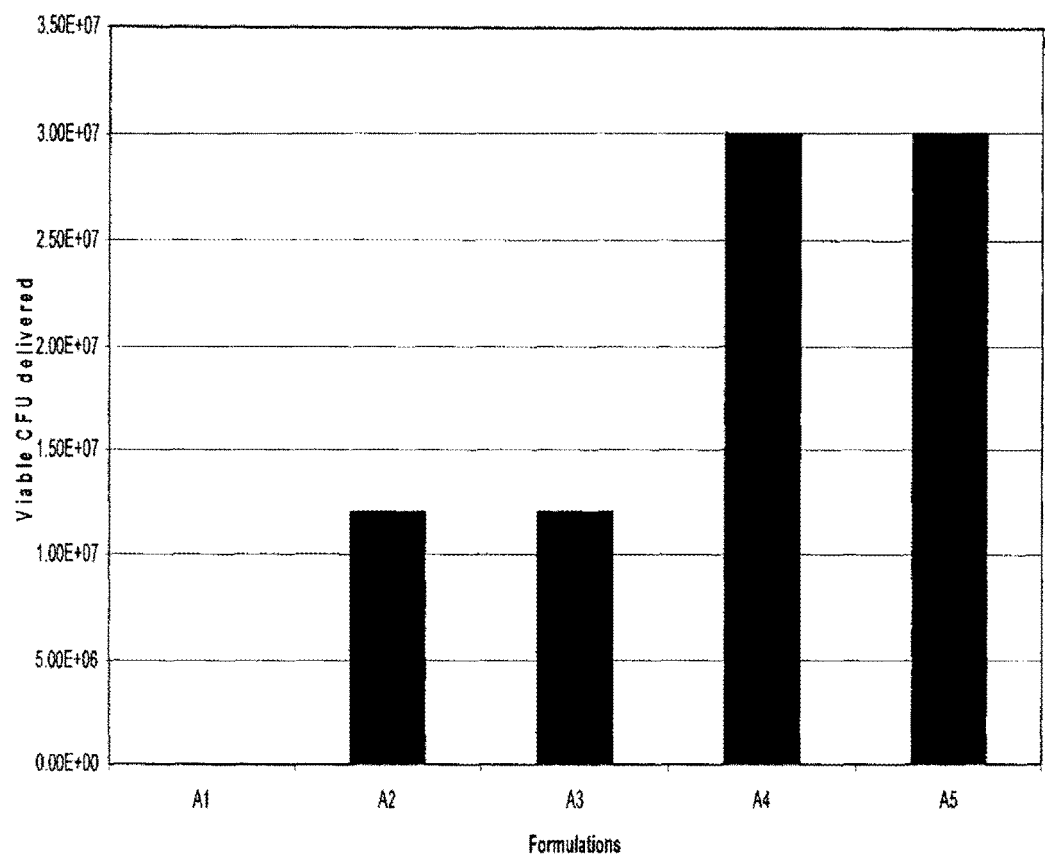
FIG. 2 shows the effects of hydrophilic agents on the controlled release of viable beneficial microorganisms into the small intestine from a prior art formulation that could be newly adapted and used to form one side of a bi-layer dosage form.

As shown in FIG. 2, the results of this example reflect a level of controlled release from a separate side of the bi-layer dosage form granted through the use of a matrix comprised of a hydrophilic agent and the lyophilized probiotic. This controlled release is shown through a much higher level of viable lactic acid bacteria colony forming units (CFU) delivered after exposure to gastric media than the control. The use of less swellable hydrophilic agents such as MCC and maltodextrin are associated with sufficient, but lower levels of control. A superior level of control is demonstrated in both polyethylene oxide and HPMC matrices. Thus, the hydrophilic agent is not limited to a particular type of hydrophilic agent, so long as sufficient matrix viscosity is achieved.

TABLE 4

| Dosage Formulas (mg) | A1 (CTRL) | A2 (Negative Control) | A3 (Negative Control) | A4 | A5 |
|---|---|---|---|---|---|
| Lactic acid bacteria pre-blend | 150 | 150 | 150 | 150 | 150 |
| HPMC | 0 | 0 | 0 | 200 | 0 |
| PEO | 0 | 0 | 0 | 0 | 200 |
| MCC | 0 | 200 | 0 | 0 | 0 |
| Maltodextrin | 0 | 0 | 200 | 0 | 0 |
| Stearic Acid | 16 | 16 | 16 | 16 | 16 |
| Silica | 16 | 16 | 16 | 16 | 16 |
| TOTAL WEIGHT | 182 | 382 | 382 | 382 | 382 |

Example 5

One side of a bi-layer dosage form as a tablet, approximately 382 mg, containing a hydrophilic agent, an electrolytic agent, and a probiotic pre-blend may be prepared as shown in Table 5. The group B1 is the control. The formulation employs HPMC as the hydrophilic agent. The electrolytic agents used include any one of the $NaHCO_3$, $Na_2CO_3$ or $NaH_2PO_4$. The probiotic, in this case, consists of lactic acid bacteria pre-blend of lyophilized powder and starch. The addition of the electrolytic agent, any one of $NaHCO_3$, $Na_2CO_3$ or $NaH_2PO_4$, establishes the internal pH within the dosage form of the delivery system. Stearic acid is included as a flow agent and silica is employed as flow agent and desiccant.

Figure 3:
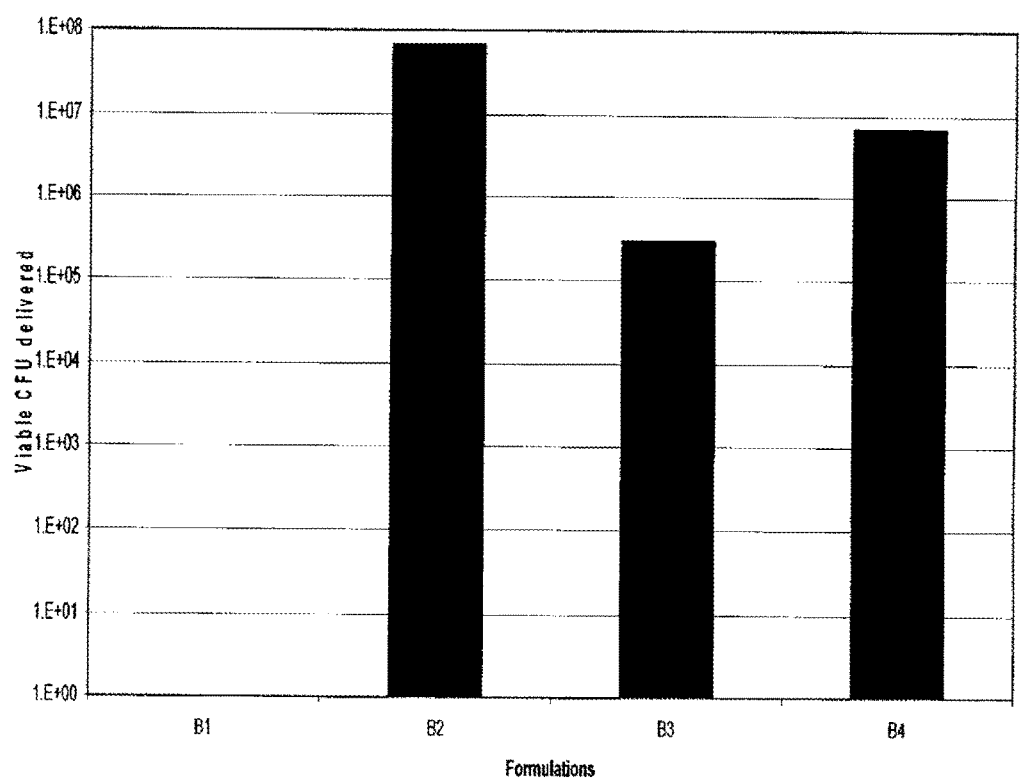
FIG. 3 shows the effects of the addition of electrolytic agents on the controlled release of viable beneficial microorganisms into the small intestine from a prior art formulation that could be newly adapted and used to form one side of a bi-layer dosage form.

This example demonstrates, as shown in FIG. 3, that the internal pH of a separate side of the bi-layer dosage form is altered by the presence of the electrolytic agent, affecting the amount of viable CFU delivered. This establishment of a particular internal pH is associated with differing levels of viability for a given reconstituted lyophilized BC. In particular, formulation B2 contains $Na_2CO_3$ and the electrolytic agent provides an internal pH within the dosage form of the delivery system and aids in the reconstitution of viable lactic acid bacteria.

TABLE 5

| Dosage Formulas (mg) | B1 (ctrl) | B2 | B3 | B4 |
|---|---|---|---|---|
| Lactic acid bacteria pre-blend | 150 | 150 | 150 | 150 |
| HPMC | 00 | 100 | 100 | 100 |
| MCC | 200 | 0 | 0 | 0 |
| $Na_2CO_3$ | 0 | 100 | 0 | 0 |
| $NaHCO_3$ | 0 | 0 | 100 | 0 |
| $NaH_2PO_4$ | 0 | 0 | 0 | 100 |
| Stearic Acid | 16 | 16 | 16 | 16 |
| Silica | 16 | 16 | 16 | 16 |
| TOTAL WEIGHT | 382 | 382 | 382 | 382 |

Example 6

One side of a bi-layer dosage form as a tablet, approximately 382 mg, containing a hydrophilic agent, a release-modifying agent, and a probiotic pre-blend may be prepared as shown in Table 6. The group C1 is the control. The hydrophilic agent employed is HPMC. The release-modifying agent employed is pectin or gelatin. The lactic acid bacteria pre-blend of lyophilized powder and starch makes up the BC. Stearic acid is included as a flow agent and silica is employed as flow agent and desiccant.

Figure 4:
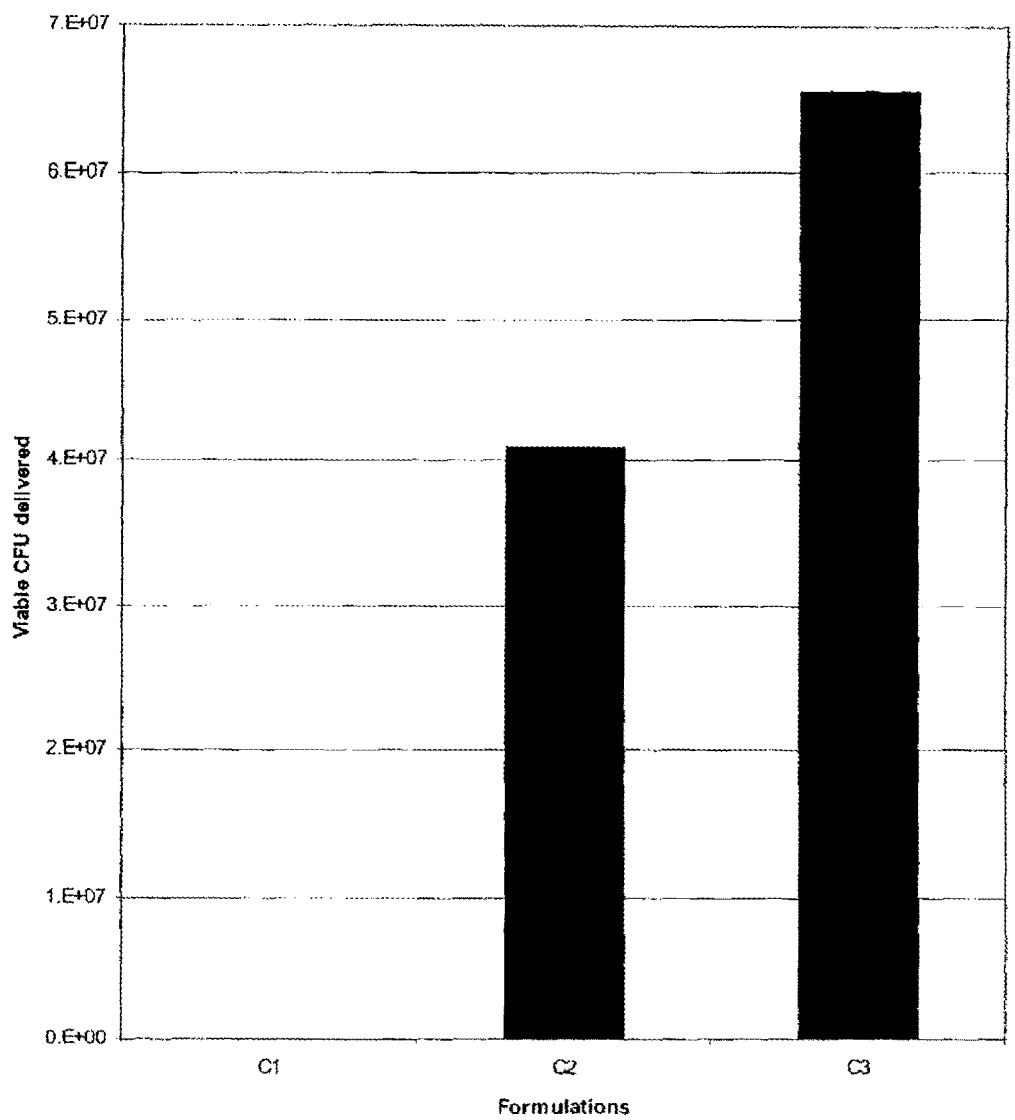
FIG. 4 shows the effects of the addition of pH and enzyme-sensitive agents on the controlled release of viable beneficial microorganisms into the small intestine from a prior art formulation that could be newly adapted and used to form one side of a bi-layer dosage form.

This example illustrates, as shown in FIG. 4, an increased level of control that is possible when the release modifying agent is added to a hydrophilic swellable matrix. The presence of pectin or gelatin as the release modifying agent is associated with a degree of pH-dependent degradation and an overall increase in matrix viscosity which retards the release of the probiotic. This is reflected in the increase in viable CFU delivered after exposure to the gastric pH media.

TABLE 6

| Dosage Formulas (mg) | C1 (CTRL) | C2 | C3 |
| --- | --- | --- | --- |
| Lactic acid bacteria pre-blend | 150 | 150 | 150 |
| HPMC | 0 | 100 | 100 |
| MCC | 200 | 0 | 0 |
| Pectin | 0 | 100 | 0 |
| Gelatin | 0 | 0 | 100 |
| Stearic Acid | 16 | 16 | 16 |
| Silica | 16 | 16 | 16 |
| TOTAL WEIGHT | 382 | 382 | 382 |

Example 7

One side of a bi-layer dosage form as a tablet, approximately 534 mg, containing a hydrophilic agent, an electrolytic agent, a release-modifying agent, an inert filler, and a probiotic pre-blend was prepared as shown in Table 7. The hydrophilic agent employed is HPMC. The electrolytic agent used is NaHCO$_3$. The release-modifying agent employed is pectin, and the inert filler employed is MCC. The probiotic pre-blend employed in this example consists of the lactic acid bacteria pre-blend of lyophilized powder and starch. The addition of inert filler is associated with increased power flowability which is often advantageous during the manufacturing process. Stearic acid is included as a flow agent, and silica is employed as a flow agent and desiccant. Turmeric is included as a colorant.

Figure 5:
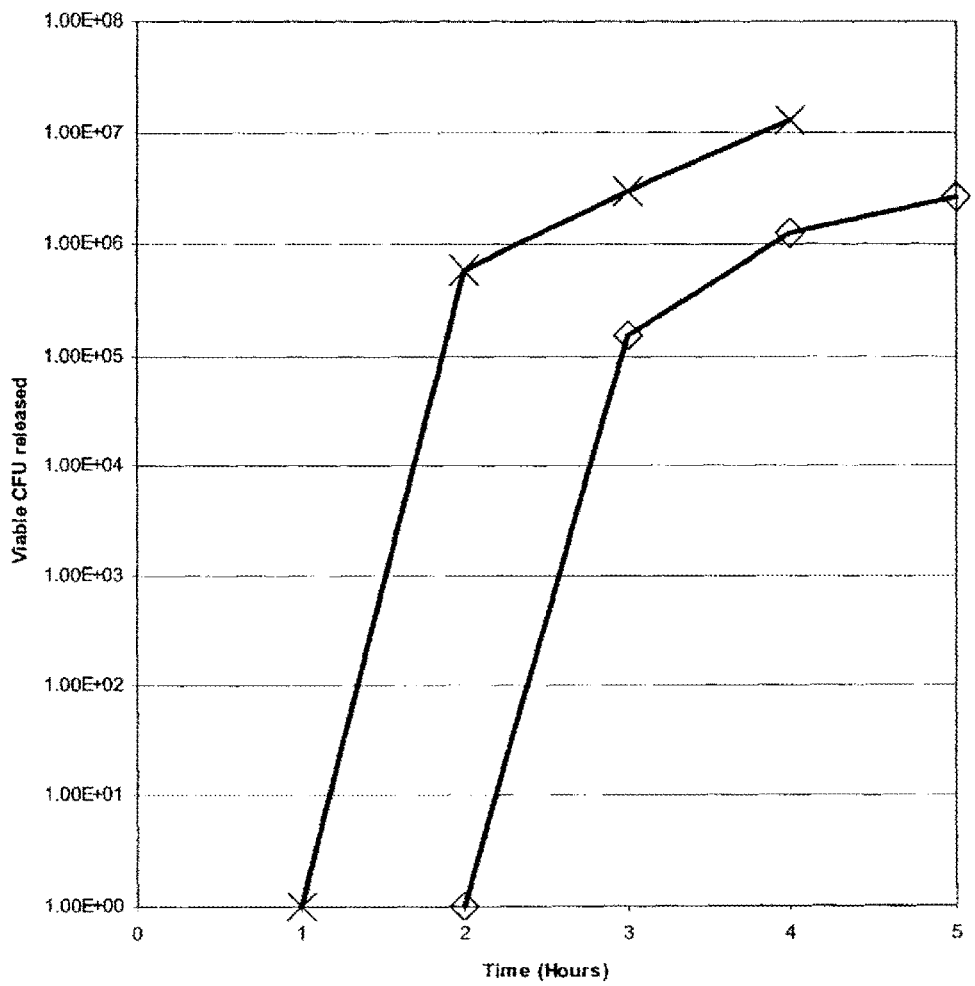
FIG. 5 shows the capacity for the controlled release of viable beneficial microorganisms over extended durations from a prior art formulation that could be newly adapted and used to form one side of a bi-layer dosage form.

As depicted in FIG. 5, the results of this example demonstrate the capacity for the controlled release of viable probiotic bacteria over an extended duration. The controlled release of the hydrophilic matrix is also shown to perform similarly regardless of the duration of exposure to gastric media. E1 and E2 are identical formulations showing the difference in controlled release based upon a 1 hour, or 2 hour exposure time, respectively.

TABLE 7

| Dosage Formulas (mg) | E1 | E2 |
| --- | --- | --- |
| Lactic acid bacteria pre-blend | 150 | 150 |
| HPMC | 50 | 50 |
| NaHCO$_3$ | 50 | 50 |
| MCC | 200 | 200 |
| Pectin | 50 | 50 |
| Stearic Acid | 16 | 16 |

TABLE 7-continued

| Dosage Formulas (mg) | E1 | E2 |
| --- | --- | --- |
| Silica | 16 | 16 |
| Turmeric | 2 | 2 |
| TOTAL WEIGHT | 534 | 534 |

Example 8

One side of a bi-layer dosage form as a tablet, approximately 532 mg, containing a hydrophilic agent, an electrolytic agent, a release-modifying agent, an inert filler, and a probiotic pre-blend was prepared as shown in Table 8. The hydrophilic agent employed is HPMC or PEO. The electrolytic agent used is NaHCO$_3$. The release-modifying agent employed is pectin, and the inert filler employed is MCC. The probiotic employed in this example consists of the *bifidobacterium* pre-blend of lyophilized powder and starch. Stearic acid is included as a flow agent, and silica is employed as a flow agent and desiccant. Turmeric is included as a colorant.

Figure 6:
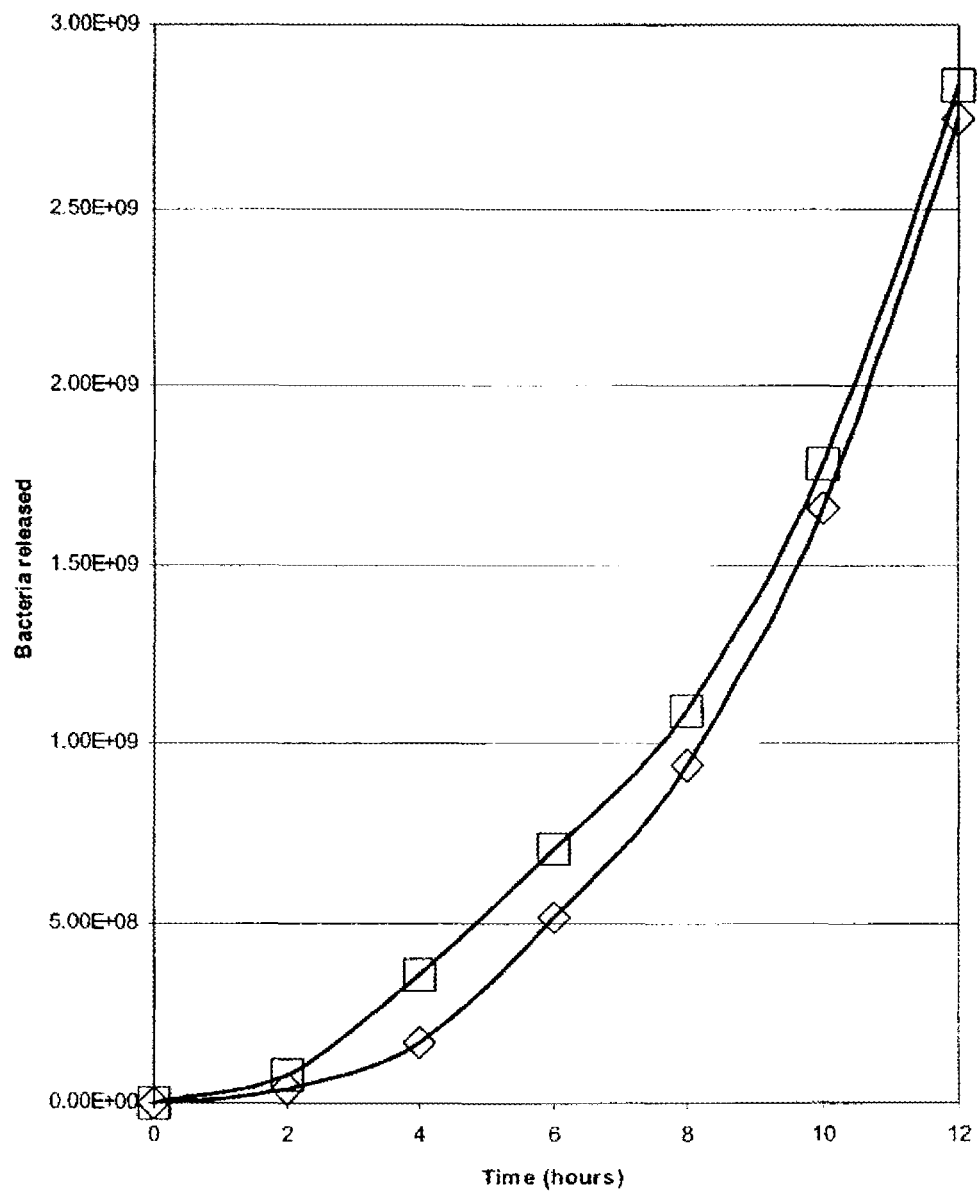
FIG. 6 shows the controlled release of beneficial microorganisms specific to the lower intestinal tract over an extended duration of 12 hours from a prior art formulation that could be newly adapted and used to form one side of a bi-layer dosage form.

As depicted in FIG. 6, the results of this example demonstrate the capacity for the controlled release of probiotics over an extended duration. The controlled release of the hydrophilic matrix is also shown to release in a profile favorable for the delivery of the BC, in this case consisting of *bifidobacterium*, after eight hours. Such an example would be useful for delivering the *bifidobacterium* to the lower intestine and beyond the lower intestine.

TABLE 8

| Dosage Formulas (mg) | F2 | F3 |
| --- | --- | --- |
| *Bifidobacterium* bacteria pre-blend | 150 | 150 |
| HPMC | 150 | 0 |
| PEO | 0 | 150 |
| Pectin | 100 | 100 |
| NaHCO$_3$ | 100 | 100 |
| Stearic Acid | 16 | 16 |
| Silica | 16 | 16 |
| TOTAL WEIGHT | 532 | 532 |

Example 9

Single sides of a bi-layer dosage form as a tablet, approximately 684 mg and 342 mg, respectively, containing a hydrophilic agent, an electrolytic agent, a release-modifying agent, an inert filler, and a probiotic pre-blend were prepared as shown in Table 9. The hydrophilic agent employed is HPMC. The electrolytic agent employed is NaHCO$_3$. The release-modifying agent employed is pectin. The probiotic pre-blend employed in this example consists of the lactic acid bacteria pre-blend of lyophilized powder and starch. Stearic acid is included as a flow agent, and silica is employed as a flow agent and desiccant.

Figure 7:
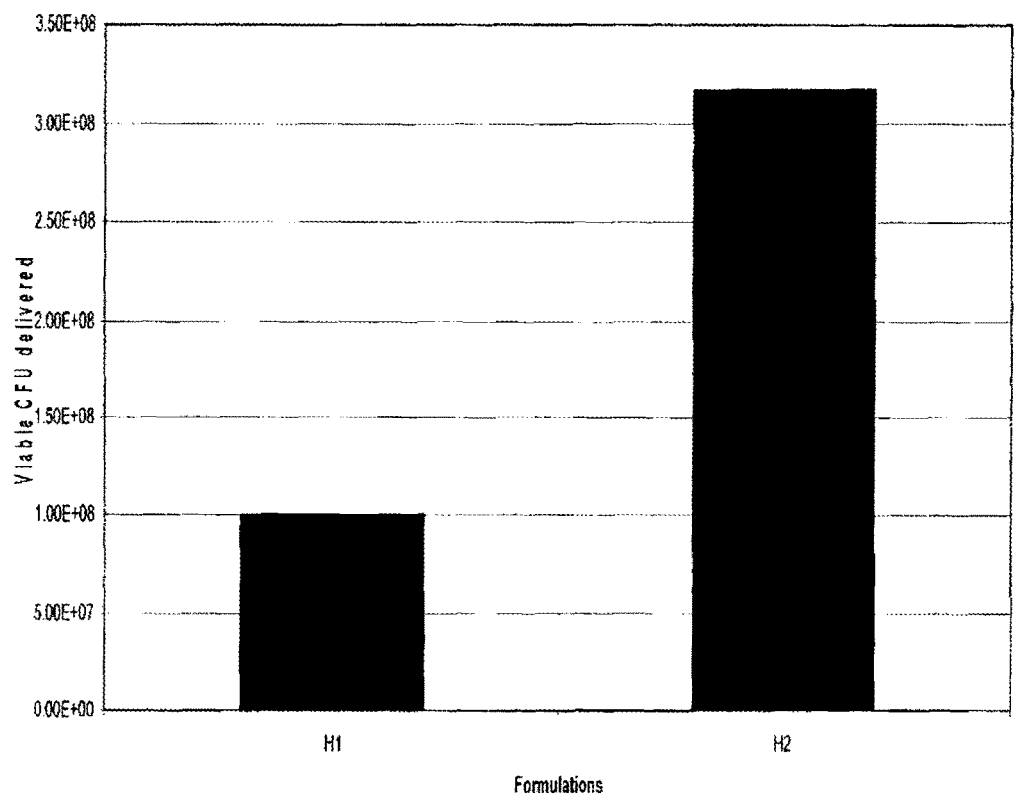
FIG. 7 shows the capacity for controlling geometric scalability, tablet size and shape variation in the present invention and the effect of such changes on the controlled release of viable beneficial microorganisms into the small intestine from a prior art formulation that could be newly adapted and used to form one side of a bi-layer dosage form.

The results of this example, as depicted in FIG. 7, demonstrate that the combination of the hydrophilic agent, the electrolytic agent, and the release-modifying agent is capable of controlling geometric scalability, tablet shape, size and volume while controlling the release of the probiotic from the delivery system in its hydrophilic matrix and dosage form of a monolithic tablet. This flexibility of varying the dosage form is especially useful in manufacturing when differing formulation volumes is required, particularly altering tablet shapes and sizes.

TABLE 9

| Dosage Formulas (mg) | H1 | H2 |
|---|---|---|
| Lactic acid bacteria pre-blend | 75 | 150 |
| Pectin | 50 | 100 |
| HPMC | 50 | 100 |
| NaHCO$_3$ | 50 | 100 |
| Guar | 100 | 200 |
| Stearic Acid | 8 | 16 |
| Silica | 8 | 16 |
| Turmeric | 1 | 2 |
| TOTAL WEIGHT | 342 | 684 |

Example 10

One side of a bi-layer dosage form as a tablet, approximately 684 mg, containing a hydrophilic agent, an electrolytic agent, a release-modifying agent, an inert filler, and a probiotic pre-blend was prepared as shown in Table 10. The hydrophilic agent employed is HPMC. The electrolytic agent used is NaHCO$_3$. The release-modifying agent employed is pectin, and the inert filler employed is MCC. The probiotic employed in this example consists of the lactic acid bacteria pre-blend of lyophilized powder and starch. Stearic acid is included as a flow agent, and silica is employed as a flow agent and desiccant. Turmeric is included as a colorant.

Figure 8:
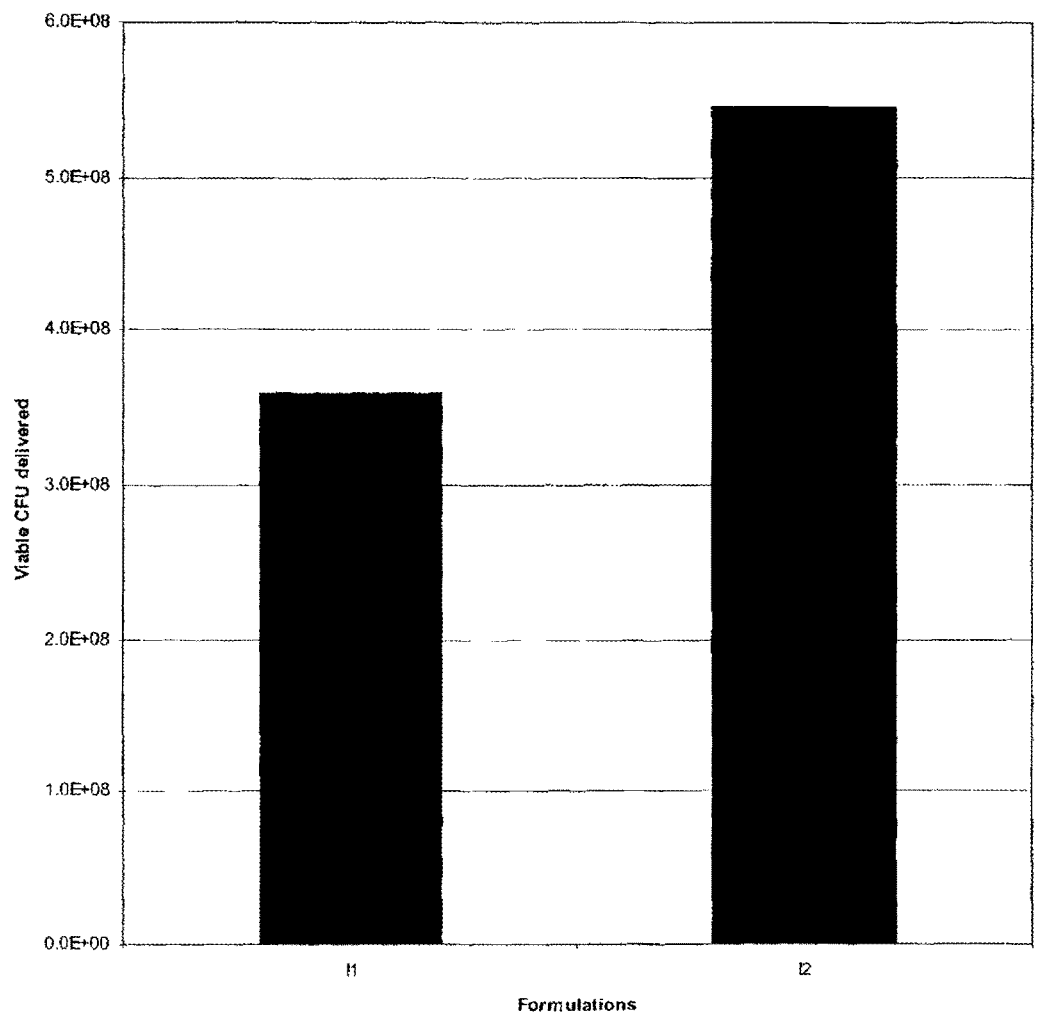
FIG. 8 shows the effects of drying the agents prior to tableting on the controlled release of viable beneficial microorganisms into the small intestine from a prior art formulation that could be newly adapted and used to form one side of a bi-layer dosage form.

The results of this example, as depicted in FIG. 8, demonstrate the application of drying an identical formulation of excipients of a pre-blend before tableting (I2) vs. a non-dried pre-blend (I1). The beneficial effects of drying are evidenced by the increase in viable lactic acid bacteria or probiotic CFU delivered in the dried pre-blend, I2, when compared to the non-dried pre-blend, I1.

TABLE 10

| Dosage Formulas (mg) | I1 | I2 |
|---|---|---|
| Lactic acid bacteria pre-blend | 150 | 150 |
| HPMC | 100 | 100 |
| Pectin | 100 | 100 |
| NAH(CO3)2 | 100 | 100 |
| MCC | 200 | 200 |
| Stearic Acid | 8 | 8 |
| Silica | 8 | 8 |
| Turmeric | 2 | 2 |
| TOTAL WEIGHT | 684 | 684 |

Example 11

One side of a bi-layer dosage form as a tablet, approximately 532 mg, containing a hydrophilic agent, an electrolytic agent, a release-modifying agent, an inert filler, and a probiotic pre-blend was prepared as shown in Table 11. The hydrophilic agent employed is HPMC of viscosity 4000 mPa (H1) or 15000 mPa (H2). The electrolytic agent employed is NaHCO$_3$. The release-modifying agent employed is pectin, and the inert filler employed is MCC. The probiotic pre-blend employed in this example consists of the *bifidobacterium* pre-blend of lyophilized powder and starch. Stearic acid is included as a flow agent, and silica is employed as a flow agent and desiccant. Turmeric is included as a colorant.

Figure 9:
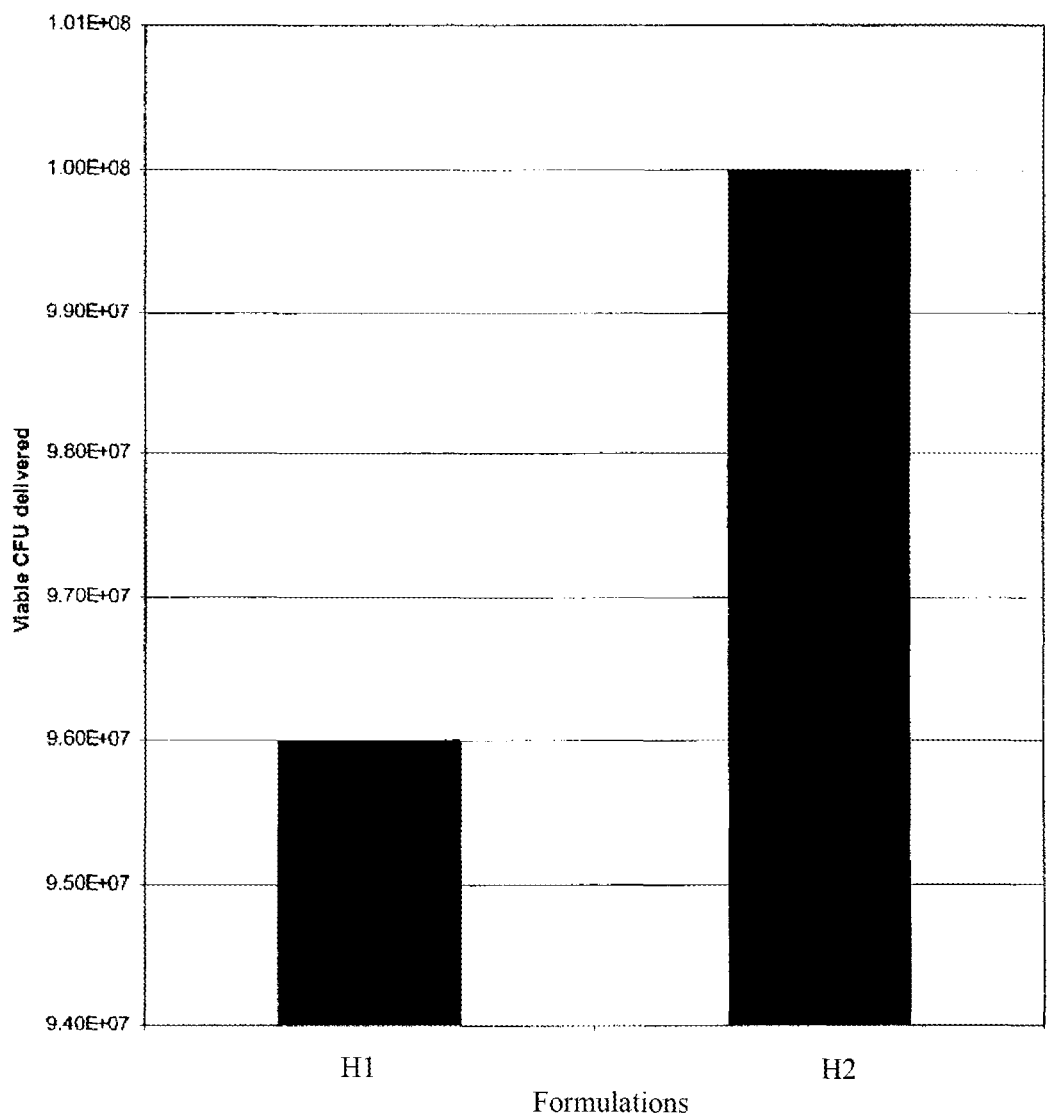
FIG. 9 shows the effects of a hydrophilic matrix employing hydrophilic agents of differing viscosities on the controlled release of viable beneficial microorganisms into the small intestine from a prior art formulation that could be newly adapted and used to form one side of a bi-layer dosage form.

As depicted in FIG. 9, the results of this example demonstrate the capacity for differentially controlled release of viable probiotics by employing hydrophilic agents of differing viscosities.

TABLE 11

| Dosage Formulas (mg) | H1 | H2 |
|---|---|---|
| Lactic acid bacteria pre-blend | 75 | 75 |
| HPMC, 4000 mPa | 50 | 0 |
| HPMC, 15000 mPa | 0 | 50 |
| Pectin | 50 | 50 |
| NaHCO$_3$ | 50 | 50 |
| MCC | 100 | 100 |
| Stearic Acid | 8 | 8 |
| Silica | 8 | 8 |
| Turmeric | 1 | 1 |
| TOTAL WEIGHT | 342 | 342 |

Example 12

One side of a bi-layer dosage form as a tablet, approximately 343 mg, containing a hydrophilic agent, an electrolytic agent, a release-modifying agent, an inert filler, and a probiotic pre-blend was prepared as shown in Table 12. The hydrophilic agent employed is HPMC. The electrolytic agent employed is NaHCO$_3$. The release-modifying agent employed is pectin, and the inert filler employed is MCC. The probiotic pre-blend employed in this example consists of the lactic acid pre-blend of lyophilized powder and starch. Stearic acid is included as a flow agent, and silica is employed as a flow agent and desiccant. Turmeric is included as a colorant.

Figure 10:
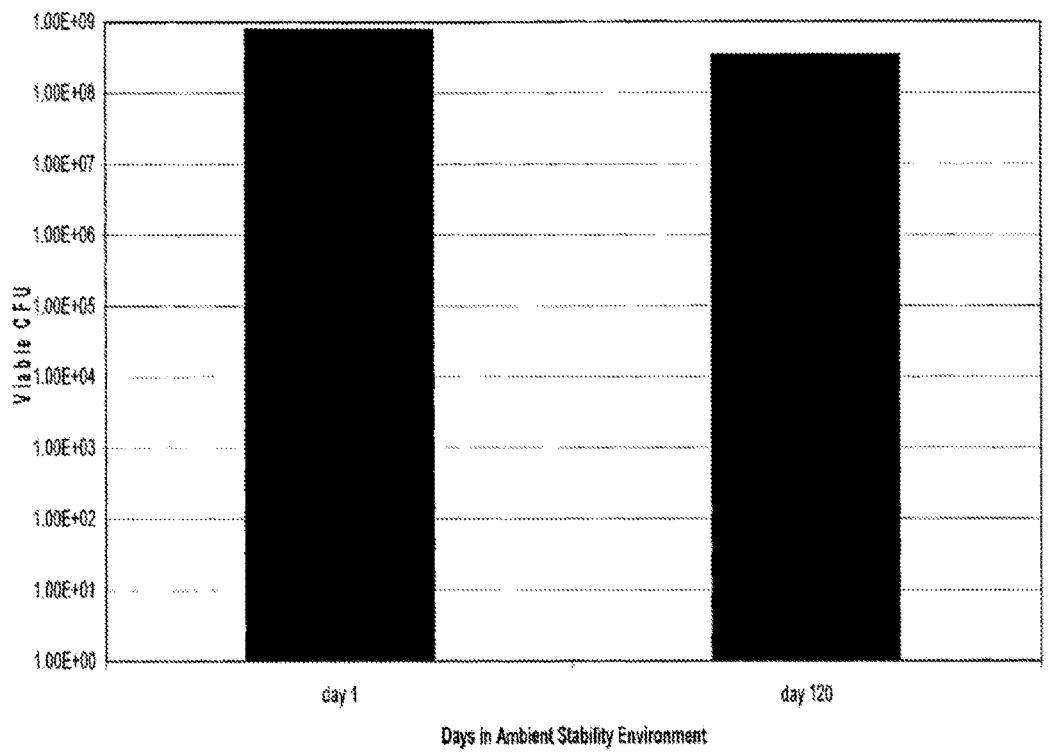
FIG. 10 shows the effects of physiologically acceptable electrolytic agents on the stability of a prior art formulation that could be newly adapted and used to form one side of a bi-layer dosage form.

As depicted in FIG. 10, the results of this example demonstrate the capacity for increased stability over time when stored in an ambient environment (25 degrees C., 60% Relative Humidity), evidenced by a relatively constant amount of viable lactic acid bacteria CFU.

TABLE 12

| Dosage Formulas (mg) | K1 |
|---|---|
| Lactic acid bacteria pre-blend | 75 |
| HPMC | 50 |
| Pectin | 50 |
| NaHCO$_3$ | 50 |
| MCC | 100 |
| Stearic Acid | 8 |
| Silica | 8 |
| Turmeric | 2 |
| TOTAL WEIGHT | 343 |

The discussion above is descriptive, illustrative and exemplary and is not to be taken as limiting the scope defined by any appended claims.

The invention claimed is:

1. A layered dosage form comprising a first layer and a second layer, characterized in that each layer comprises one or more distinct probiotics together with one or more excipient formulation components; wherein the layers share one or more identical excipient formulation components; wherein the formulation is provided as a compressed cohesive dosage form unit and wherein the first layer does not surround the second layer and the second layer does not surround the first layer.

2. The layered dosage form of claim 1, wherein the cohesive dosage form unit is a compressed bi-layer tablet or caplet dosage form.

3. The layered dosage form of claim 2, wherein the compressed bi-layer tablet or caplet dosage form is formed by sequential direct compression on a two-sided tablet press.

4. The layered dosage form of claim 1, wherein the layered dosage form does not include enteric coating.

5. The layered dosage form of claim 1, wherein the one or more identical excipient formulation components are shared whereby the relative percentage (w/w) amount of each shared component in each layer is within about 20% of the other layer.

6. The layered dosage form of claim 1, wherein the relative amounts of weights of the first layer and the second layer vary from approximately 60%:40% to 70%:30%.

7. The layered dosage form of claim 1, wherein the one or more excipient formulation components are selected from one or more of the group consisting of an hydrophilic agent; an acid protectant; a release modifying agent; and an electrolyte.

8. The layered dosage form of claim 7, wherein one or more individual layers include 5-40% hydrophilic agent; 5-40% release modifying agent; and 1-40% electrolyte.

9. The layered dosage form of claim 7, wherein the acid protectant is selected from one or more of the group consisting of: sodium carbonate; sodium bicarbonate; and sodium phosphate.

10. The layered dosage form of claim 7, wherein the hydrophilic agent is selected from one or more of the group consisting of: starches; hydrophilic gum; cellulose derivatives; polysaccharides; galactomannans; silica; aluminum silicate; magnesium silicate; aluminum magnesium silicate; sodium silicate; aluminum hydroxide; protein; polymers; hydrophilic polymers; hydroxypropyl methylcellulose; hydroxypropyl cellulose; and gums.

11. The layered dosage form of claim 10, wherein the hydrophilic agent is also a binder selected from one or more of the group consisting of: hydroxypropyl methylcellulose (HPMC); microcrystalline cellulose (MCC); guar gum; and pectin.

12. The layered dosage form of claim 1, wherein the first layer includes one or more probiotics originating from the *Lactobacillus, Enterococcus, Pediococcus*, and *Streptococcus* genera and the second layer includes one or more probiotics originating from the *Bacteroides, Bifidobacterium*, and *Eubacterium* genera.

13. The layered dosage form of claim 1, wherein all of the probiotics in the first layer are different from all of the probiotics in the second layer.

14. The layered dosage form of claim 1, comprising a probiotic selected from the group consisting of members of the genus *Lactobacillus, Bifidobacterium, Lactococcus, Enterococcus, Streptococcus, Pediococcus, Bacteroides*, and portions, fragments, components, proteins, and by-products thereof.

15. The layered dosage form of claim 14, wherein the probiotic comprises superoxide dismutase (SodA).

16. A method for making the dosage form of claim 1 comprising:
(1) including formulations comprising distinct probiotics in each of at least a first layer and a second layer;
(2) compressing the first layer and the second layer; and
(3) forming a single cohesive unit.

17. The method of claim 16, further comprising: pre-compression of one of the first layer and the second layer.

18. A method for providing targeted delivery of distinct probiotics comprising:
administering to a human or animal in need thereof the layered dosage form of claim 1.

* * * * *